United States Patent
Takayama et al.

(10) Patent No.: US 10,300,302 B2
(45) Date of Patent: May 28, 2019

(54) PARTICLE BEAM TRANSPORT SYSTEM, AND SEGMENT THEREOF

(71) Applicants: KABUSHIKI KAISHA TOSHIBA, Minato-Ku (JP); Toshiba Energy Systems & Solutions Corporation, Kawasaki-Shi (JP)

(72) Inventors: Shigeki Takayama, Yokohama (JP); Ikuo Watanabe, Kawasaki (JP); Yoshifumi Nagamoto, Yokohama (JP); Takeshi Yoshiyuki, Yokohama (JP); Takashi Yazawa, Ota (JP)

(73) Assignees: KABUSHIKI KAISHA TOSHIBA, Minato-Ku (JP); Toshiba Energy Systems & Solutions Corporation, Kawasaki-Shi (JP)

( * ) Notice: Subject to any disclaimer, the term of this patent is extended or adjusted under 35 U.S.C. 154(b) by 0 days.

(21) Appl. No.: 15/747,903

(22) PCT Filed: Jul. 7, 2016

(86) PCT No.: PCT/JP2016/070150
§ 371 (c)(1),
(2) Date: Jan. 26, 2018

(87) PCT Pub. No.: WO2017/018156
PCT Pub. Date: Feb. 2, 2017

(65) Prior Publication Data
US 2018/0214715 A1 Aug. 2, 2018

(30) Foreign Application Priority Data
Jul. 29, 2015 (JP) .................................. 2015-149706

(51) Int. Cl.
*A61N 5/10* (2006.01)
*G21K 1/093* (2006.01)
(Continued)

(52) U.S. Cl.
CPC ......... *A61N 5/1042* (2013.01); *A61N 5/1077* (2013.01); *A61N 5/1079* (2013.01);
(Continued)

(58) Field of Classification Search
CPC ...... A61N 5/1042; A61N 5/10; A61N 5/1077; G21K 1/00; G21K 1/093; G21K 1/10; G21K 5/04
(Continued)

(56) References Cited

U.S. PATENT DOCUMENTS

2004/0173763 A1* 9/2004 Moriyama ............... A61N 5/10
250/492.1
2015/0031933 A1 1/2015 Yamamoto et al.

FOREIGN PATENT DOCUMENTS

JP 9-265000 A 10/1997
JP 11-176599 A 7/1999
(Continued)

OTHER PUBLICATIONS

International Search Report dated Sep. 27, 2016, in PCT/JP2016/070150 filed Jul. 7, 2016.
(Continued)

*Primary Examiner* — Nicole M Ippolito
(74) *Attorney, Agent, or Firm* — Oblon, McClelland, Maier & Neustadt, L.L.P.

(57) ABSTRACT

Provide a particle beam transport system that contribute to reduction of construction period and cost for a particle beam treatment facility including plural treatment rooms accommodating a particle-beam irradiation equipment.
A particle beam transport system 10 includes: a main line 31 configured to transport a particle beam generated by an accelerator outward; a branch line 22 branching from the main line 31; irradiation equipments 30 (30a-30d) provided at respective ends of the branch line 22 and configured to
(Continued)

irradiate a patient with the particle beam, wherein at least a part of the main line 31 and the branch line 22 is configured as plural segments 20; and beam characteristics of the particle beam of each of the plural segments 20 are substantially equal at both ends.

8 Claims, 4 Drawing Sheets

(51) Int. Cl.
*G21K 5/04* (2006.01)
*G21K 1/10* (2006.01)
(52) U.S. Cl.
CPC ............... *G21K 1/093* (2013.01); *G21K 5/04* (2013.01); *A61N 2005/1087* (2013.01); *G21K 1/10* (2013.01)

(58) Field of Classification Search
USPC ........................ 250/396 R, 397, 492.1, 492.3
See application file for complete search history.

(56) References Cited

FOREIGN PATENT DOCUMENTS

| JP | 2006-351339 A | 12/2006 |
|---|---|---|
| JP | 4639401 B2 | 2/2011 |
| JP | 2011-50660 A | 3/2011 |
| WO | WO 2013/124975 A1 | 8/2013 |

OTHER PUBLICATIONS

English translation of the International Preliminary Report on Patentability and Written Opinion dated Jan. 30, 2018 in PCT/JP2016/070150.

* cited by examiner

PARTICLE BEAM TRANSPORT SYSTEM, AND SEGMENT THEREOF

FIELD

Embodiments of the present invention relate to a particle beam transport system for transporting a particle beam from an accelerator to irradiation equipment in a treatment room and a segment thereof.

BACKGROUND

There is widely known a particle beam treatment technique in which treatment is performed by irradiating a lesion tissue (cancer) of a patient with a particle beam such as a carbon ion beam. According to this particle beam treatment technique, since it is possible to kill only a lesion tissue at pinpoint without damaging normal tissues, it is less burdensome on a patient than other treatment such as surgery and medication therapy, and thus it can be expected to accelerate social reintegration after treatment. Hence, interest in particle beam treatment has increased, and it is desired to add treatment facilities in order to cope with an increase in the number of patients who desire the particle beam treatment.

A particle beam treatment facility is large-scale including an accelerator for generating a particle beam. Thus, in order to reduce treatment cost and improve treatment throughput, it is under consideration to provide plural treatment rooms and branch a particle beam transport system such that the particle beam transport system is connected to the respective treatment rooms.

When plural treatment rooms are provided in a particle beam treatment facility, in addition to the case where these treatment rooms are arranged in the horizontal direction with respect to the substantially circular extended surface of the accelerator, there are cases where these treatment rooms are arranged in the direction perpendicular to this extended surface. Additionally, the particle beam transport system includes a main line for transporting a particle beam generated by its accelerator to the outside, and further includes a branch line that branched off from the main line to introduce particle beams into the respective treatment rooms.

CITATION LIST

Patent Literature

[PTL 1] Japanese Patent No. 4639401
[PTL 2] Japanese Unexamined Patent Application Publication No. H11-176599

SUMMARY

Technical Problem

In the case of introducing a particle beam into each of the plural treatment rooms arranged at different positions as described above, it is necessary to extend, branch, and bend the particle-beam transport line according to the layout of these treatment rooms.

The particle-beam transport line is provided with bending electromagnets and focus electromagnets for controlling the traveling direction of the particle beam.

The distribution of the charged particles in the beam passing through the line is not constant, and its cross-sectional shape varies with time because the charged particles oscillate at a constant period called betatron oscillation.

For this reason, the particle-beam transport line is required to have a design specification corresponding to the cross-sectional shape of the passing particle beam. Thus, as the line length or the number of branches of the particle-beam transport line increases, the time required for beam line design and field adjustment increases exponentially, resulting in an increase in construction period and cost.

Although a cross-sectional shape of a particle beam immediately after being extracted from an accelerator varies depending on the extraction conditions and the beam energy, the particle beam immediately after the extraction has an elliptical cross-sectional shape in most cases.

In the case of bending a particle beam that has an elliptical cross-section in a plane including the major axis of the elliptical cross-section, a magnetic field generating Lorentz force is applied from the minor axis direction of the elliptical cross-section. Additionally, in the case of bending this particle beam in a plane including the minor axis of the elliptical cross-section, the magnetic field is applied from the major axis direction of the elliptical cross-section.

In this context, a facing interval between a pair of magnetic poles constituting a bending electromagnet is determined on the basis of width of the passing particle beam. In general, the magnetic field strength decreases as the magnetic pole interval increases. Thus, in the case of transporting a particle beam with an elliptical cross-section, specifications of the bending electromagnets configured to efficiently generate a magnetic field and its control specification are different depending on the bending direction, and these specifications are easy to subdivide. This makes designing and manufacturing of equipment and/or field adjustment more complicated for a system having many branches of a particle-beam transport line.

In view of the above-described circumstances, an object of embodiments of the present invention is to provide a particle beam transport system that facilitates beamline design, design and manufacture of equipment, field adjustment, and extension and reconstruction so as to contribute to reduction of construction period and cost by making it possible to easily transport a high-quality beam to an arbitrary location in a particle beam treatment facility provided with plural treatment rooms accommodating a particle-beam irradiation equipment and to provide its segment.

DESCRIPTION OF EMBODIMENT

Hereinafter, a particle beam transport system according to an embodiment of the present invention will be described with reference to the accompanying drawings. In the drawings, the space is represented by a three-dimensional coordinate system in which the u-v plane includes a surface of an accelerator 13 and the direction orthogonal to this u-v plane is defined as the w-direction. Further, the traveling direction of a particle beam is defined as the s-direction, and the respective two directions being orthogonal to the s-direction and being orthogonal to each other are defined as the x-direction and the y-direction.

Figure 1:
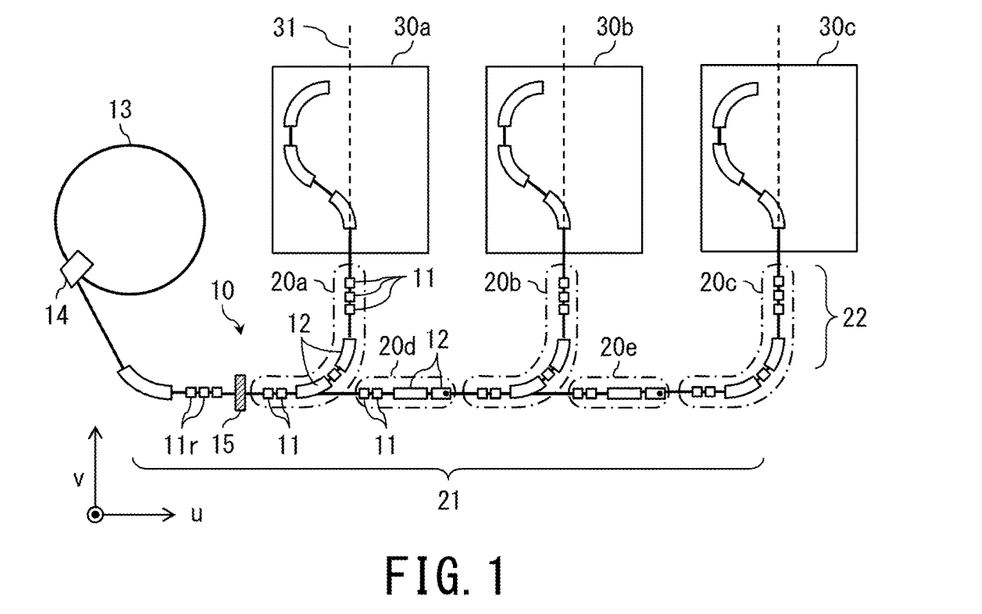
FIG. 1 is an external view of a particle beam transport system according to an embodiment of the present invention from the direction in which an accelerator can be seen in a plan view.
Figure 2:
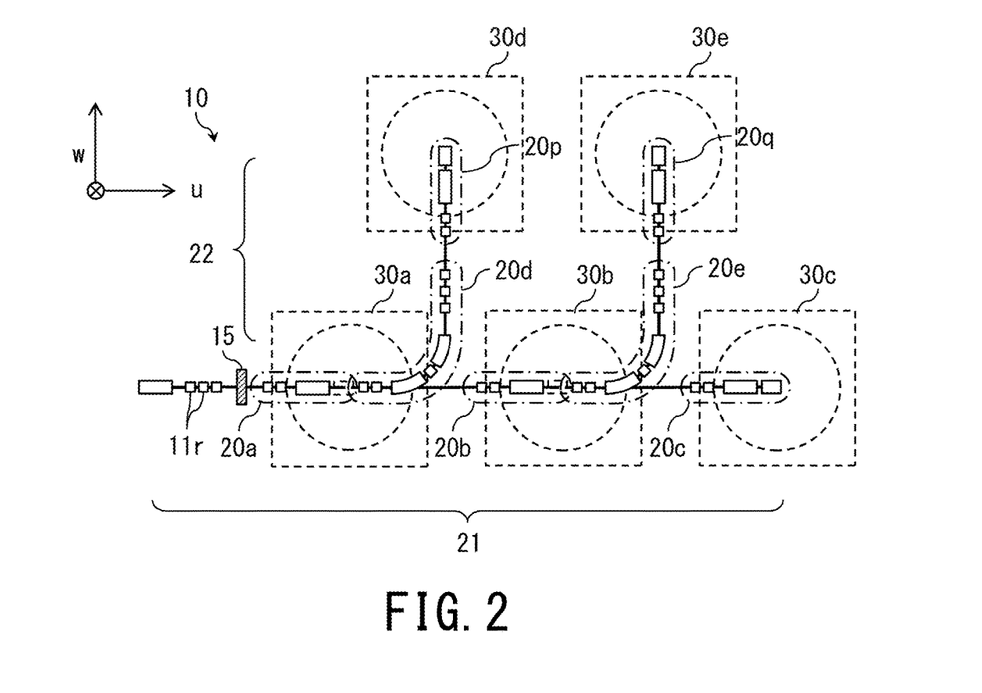
FIG. 2 is an external view of the particle beam transport system according to the embodiment from such a direction along a rotation axis of a gantry-type irradiation equipment that the accelerator can be viewed from the side.
Figure 3:
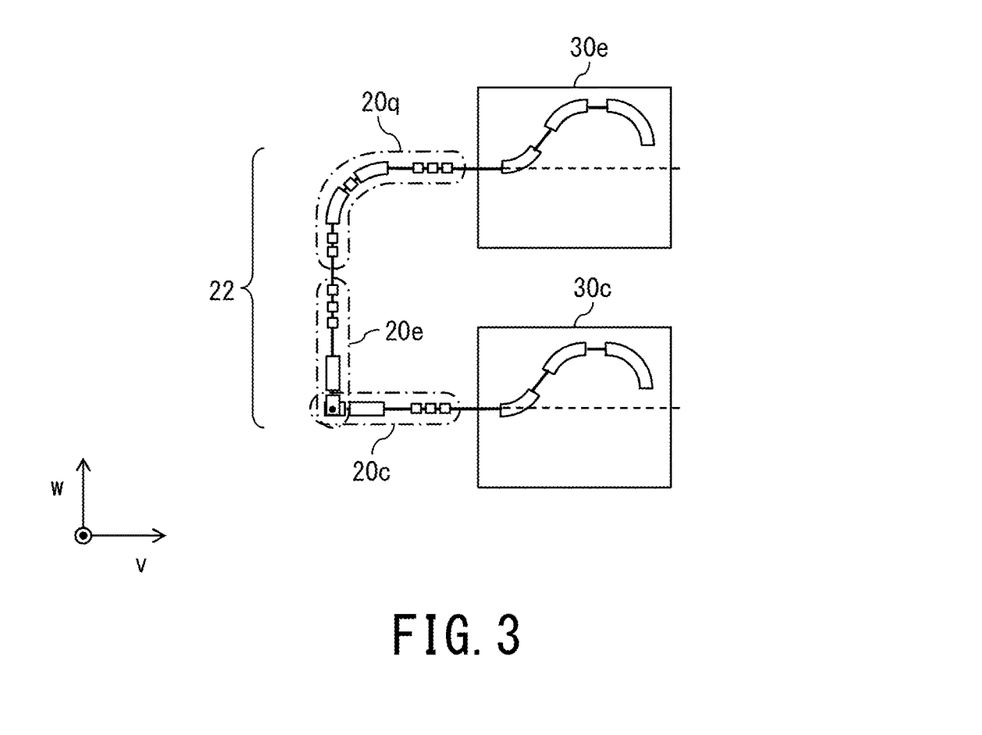
FIG. 3 is an external view of the particle beam transport system according to the embodiment from such a direction perpendicular to the rotation axis of the gantry-type irradiation equipment that the accelerator can be viewed from the side.

As shown in FIG. 1 to FIG. 3, a particle beam transport system 10 includes focus electromagnets 11 for converging the outer diameter of a passing particle beam by the action of a magnetic field, bending electromagnets 12 for bending the traveling direction of the passing particle beam by the action of a magnetic field, a main line 21 for transporting the particle beam generated by an accelerator 13 to the outside, and a branch line 22 that branches off from the main line 21. At the respective ends of the branch line 22, irradiation equipments 30 (30a to 30e) for irradiating a patient with a particle beam are provided. The main line 21 and the branch line 22 are composed of two or more segments 20 (20a to 20e, 20p, 20q) in which the arrangement of the focus electromagnets 11 and the bending electromagnets 12 is common. Each segment 20 is configured in terms of component arrangement such that each segment 20 can make the particle beam at its segment entrance and the particle beam at its segment exit the same in terms of characteristics. Further, in the particle beam transport system 10, a scatterer 15 for multiple scattering of the passing particle beam is provided at the upstream of the segment 20a nearest to the accelerator 13 such that the cross-section of the particle beam is substantially circular at both ends. A characteristic of the particle beam is physical quantity representing the state of the particle beam, and means, e.g., a betatron function β, an α function, dispersion, change rate of dispersion, and emittance.

The main line 21 and the branch line 22 are enclosed continuous spaces having a degree of vacuum sufficient to pass the particle beam.

The accelerator 13 is, e.g., a synchrotron, and causes a particle beam, which is generated by accelerating charged particles such as $C^{6+}$ generated by an ion generating source (not shown) to about 70 to 80% of the light velocity, to be emitted from an exit deflector 14 to the main line 21.

A particle beam decreases its speed by losing kinetic energy when passing through a body of a patient, and suddenly stops when falling to a certain speed by receiving a resistance that is approximately inversely proportional to the square of speed. In the vicinity of the stop point of the particle beam, high energy called Bragg peak is emitted.

In the particle beam treatment technique, treatment is performed by adjusting this Bragg peak to a lesion tissue of a patient while damage on normal tissues is being reduced.

The particle beam emitted from the accelerator 13 has non-uniform distribution of charged particles in a cross-section perpendicular to the traveling direction, and oscillates at a constant period as it is called betatron oscillation. Thus, the particle beam emitted from the accelerator 13 varies in characteristics, and its cross-sectional shape to be observed changes with respect to the beam traveling direction. Since components were designed, manufactured, arranged, and controlled according to the beam characteristics in conventional technology in order to efficiently control the above-described particle beam, there was a problem that specifications and its control became subdivided and field adjustment work became complicated together with an increase in the type of equipment. This problem is solved as described below.

Figure 4:
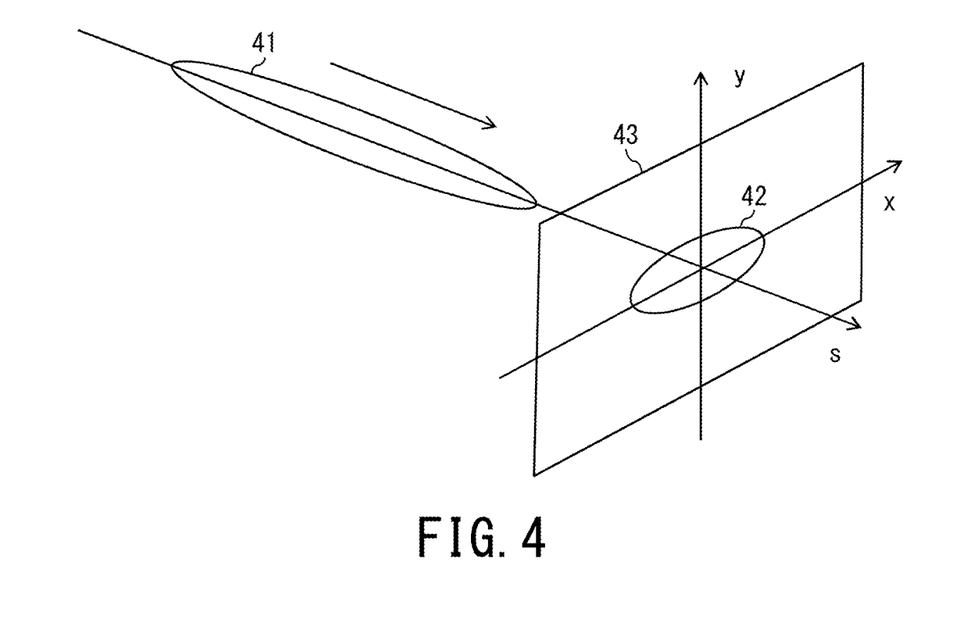
FIG. 4 is an observation diagram of a particle beam and its cross-sectional shape.

As shown in FIG. 4, the cross-sectional shape 42 indicates spread of the beam in the x-y plane that is perpendicular to the traveling direction s of the particle beam 41.

The cross-sectional shape 42 can be observed by disposing a screen monitor 43 in the beam traveling direction s and detecting intensity distribution and the like of the beam in the plane.

Figure 5:
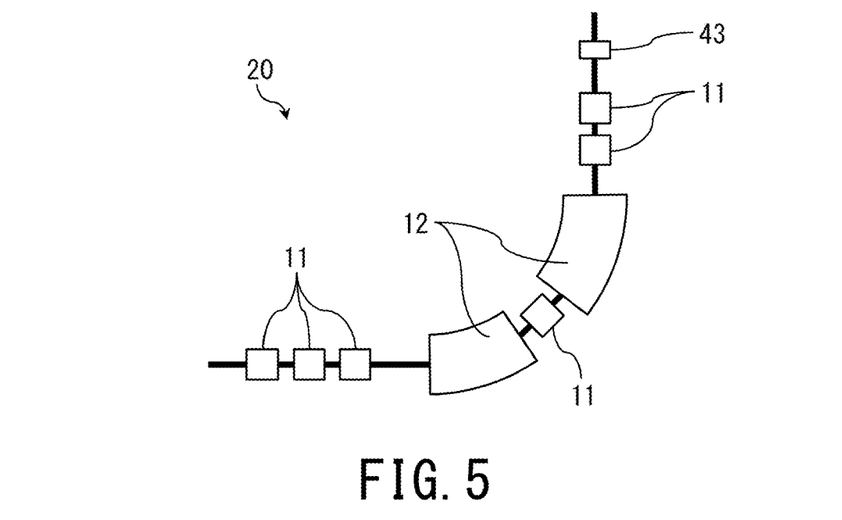
FIG. 5 is an external view of segments constituting the particle beam transport system according to the embodiment.

As shown in FIG. 5, each segment 20 includes the focus electromagnets 11, the bending electromagnets 12, a beam-trajectory correction electromagnet (not shown), the screen monitor 43, and a vacuum duct (not shown). In each segment 20, the sequence, placement position, and arrangement angle of its components are determined such that the characteristics and cross-sectional shape of the particle beam are substantially the same at both ends. Further, beam adjustment is performed for each segment 20 by the screen monitor 43 arranged at the most downstream in each segment 20. Each segment 20 shown in the embodiment has a function of bending and transporting the particle beam at an angle of 90° with respect to the traveling direction. In addition, the cross-sectional shape of the particle beam is substantially circular at both ends.

Thus, by joining the plural segments 20 to each other, it is possible to easily deflect the trajectory of the particle beam in multiple stages in the horizontal direction and in the vertical direction without newly designing the beam line and without concern for the length of the beam line and the number of branches. In this manner, it is possible to freely transport the particle beam to plural irradiation equipments 30 (30a, 30b, 30c) arranged at the same height level as the accelerator 13 and/or plural irradiation equipments 30 (30d, 30e) arranged at different height levels. In addition, since the constituent components are common to the respective segments, the number of types of components can be reduced, its management is easy, and cost reduction due to mass production effect can be expected.

Further, since field adjustment can be performed for each segment, the time required for alignment adjustment and beam adjustment is shortened. Thus, workability is improved not only at initial installation but also at the time of replacing a component due to, e.g., a trouble. In particular, the larger the system becomes in beam line length and in number of branches, the greater this effect becomes. Since each component includes errors such as manufacturing error and installation error, the arrangement and output of the components constituting the segments are finely adjusted for each segment by field adjustment such that the characteristics and cross-sectional shape of the particle beam match the designed values.

The segments 20 constitute a part or all of the main line 21 and the branch line 22. Although only one arrangement pattern for the segments 20 is shown in the embodiment, the particle beam transport system 10 may be configured by using plural arrangement patterns of segments in combination. For instance, by combining segments having a function of bending and transporting a particle beam at an angle of 45° with respect to the traveling direction, it is also possible to irradiate a patient with a particle beam from an obliquely upward direction instead of from the vertical direction.

Next, a method of controlling the cross-sectional shape of the particle beam will be described.

The bending electromagnets 12 can make the beam trajectory into an arc shape by bending the traveling direction of the passing particle beam under the action of a magnetic field. The particle beam passing through the bending electromagnets 12 is caused to go straight in a tangential direction.

Figure 7:
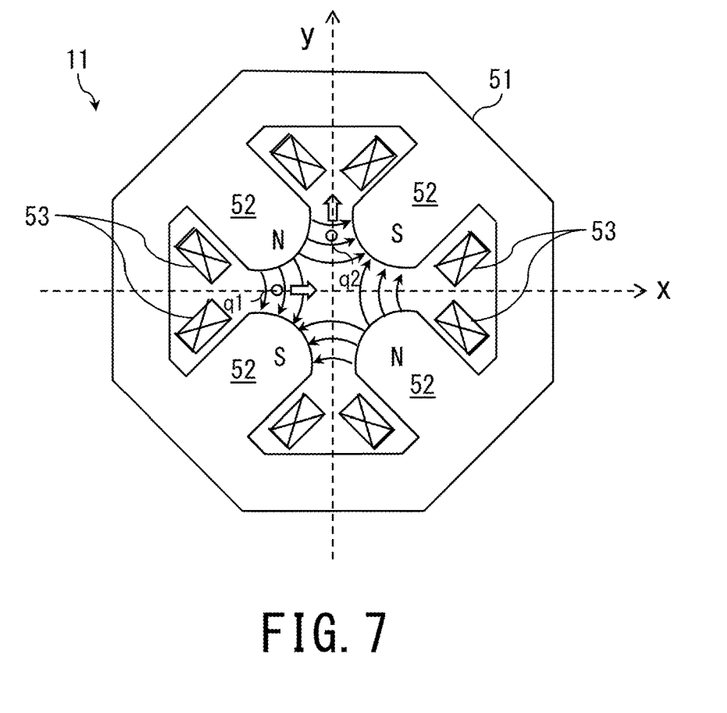
FIG. 7 is a cross-sectional view of a focus electromagnet taken along a plane (x-y plane) that is perpendicular to the beam axis.

As shown in FIG. 7, each focus electromagnet 11 includes a substantially ring-shaped yoke 51, four magnetic cores 52 integrally projected inwardly from the yoke 51 at equal angular intervals, and exciting coils 53 individually wound around the four magnetic cores 52. In the gap inside the yoke 51, magnetic fields indicated by the solid arrows are generated. Although a quadrupole electromagnet is exemplified as the focus electromagnets 11 in the embodiment, the configuration is not limited to such an aspect.

For the charged particle beam to be transported, Lorentz force in the inner direction acts on the charged particle located at q1 on the x-axis and Lorentz force in the outer direction acts on the charged particle located at q2 on the y-axis. That is, each focus electromagnet 11 focuses the particle beam in the x-axis direction and defocuses the particle beam in the y-axis direction.

Intensity of focusing/defocusing a beam can be controlled by intensity of direct current applied to the exciting coils 53.

In addition, it is possible to reverse the focus direction and defocus direction of the beam by reversing the direction of the direct current applied to the excitation coils 53, because the direction of each magnetic field to be formed is reversed by reversing the direction of the direct current.

Since the plural focus electromagnets 11 in the embodiment are configured by alternately arranging the one for focusing the beam in the x-direction and the one for focusing the beam in the y-direction, the plural focus electromagnets 11 adjust the beam diameter to a desired value by controlling the direct current applied to each electromagnet 11 and sequentially adjusting balance between focusing and defocusing in the x-direction and the y-direction.

Figure 6:
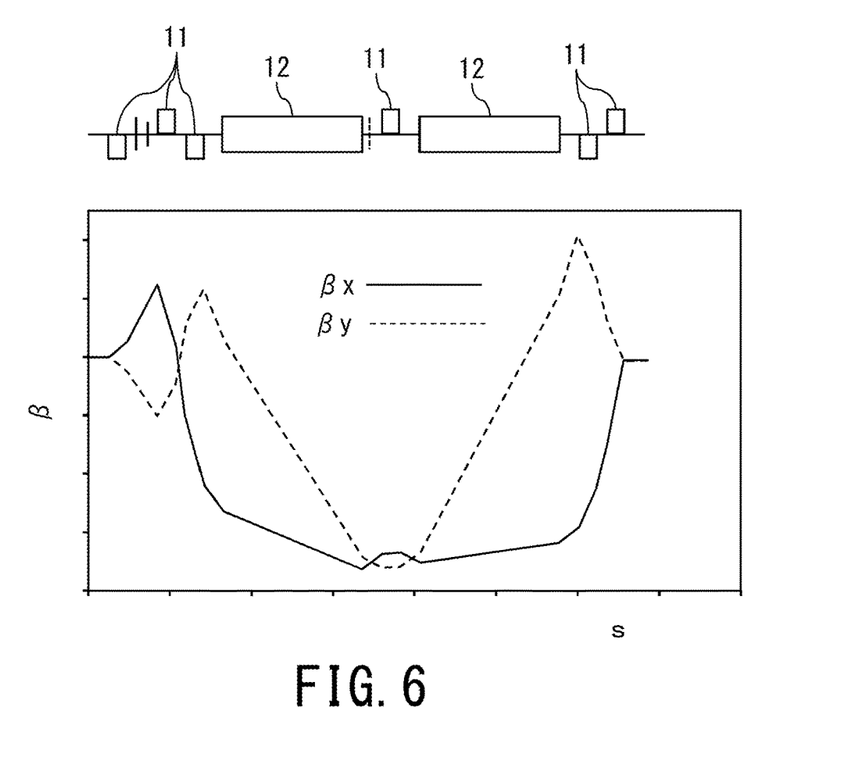
FIG. 6 is a graph illustrating parameters of a particle beam at a segment position in two directions (x-direction and y-direction) perpendicular to each other.

The graph of FIG. 6 illustrates a case where the focus electromagnets 11 and the bending electromagnets 12 constituting one segment 20 are developed on a straight line and the betatron function β of the particle beam at the position s of this segment 20 is divided into two directions (i.e., x-direction and y-direction) orthogonal to each other.

The betatron function β is a parameter related to the outer diameter of the particle beam. In order to avoid collision with the particle beam, there is a close relationship between the facing interval of a pair of magnetic poles constituting the bending electromagnet and the outer diameter of the beam. In order to efficiently generate a magnetic field without widening the interval between the magnetic poles, the betatron function β is suppressed to as small as 100 m or less.

In each segment 20 of the present embodiment, arrangement conditions of respective components including arrangement order, placement positions, and arrangement angles are determined in such a manner that the betatron function β (βx, βy) in the orthogonal direction (x, y) of the passing particle beam is equal at the upstream end and the downstream end. In the present embodiment, the first bending electromagnet 12, the quadrupole electromagnet 11, and the second bending electromagnet 12 are symmetrically arranged in this order so as not to change the dispersion before and after the deflection, and two quadrupole electromagnets 11 for controlling the betatron functions in the x-direction and the y-direction are arranged at each of its upstream side and downstream side.

This component arrangement can be variously modified according to each embodiment. For instance, when three quadrupole electromagnets are used, control of the betatron function becomes easy and it is possible to realize wide beam energy width. In addition, by arbitrarily arranging beam trajectory correction electromagnets upstream and downstream, it is possible to finely adjust the beam axis according to the local environment on a segment basis. Additionally or alternatively, by arranging a screen monitor at the most upstream and/or the most downstream, beam behavior in each segment can be grasped in detail.

Since energy of a transport beam differs depending on depth of an irradiation target, the optimum current value corresponding to the energy of the transport beam is preset for each electromagnet. In this case, the current values of the respective electromagnets in each segment are adjusted to each other in such a manner that the beam parameters such as the betatron function, dispersion and its change rate are equal at the upstream end and the downstream end. In other words, each segment 20 is configured such that the characteristics and cross-sectional shape of the particle beam are substantially the same at both ends.

In the above-described case, by setting the phase difference between the upstream end and the downstream end to be an integral multiple of 180 degrees, the phase at the end of the irradiation equipment can always be kept constant regardless of the number of segments.

It may be set to have a predetermined phase at the end of the irradiation equipment as a result of combining plural segments, but the degree of freedom of placement is reduced in such a case.

Returning to FIG. 1, the description of configuration of the particle beam transport system 10 is continued.

The scatterer 15 is provided further upstream of the segment 20a that is closest to the accelerator 13. Although a thin plate of aluminum is used for the scatterer 15 in the present embodiment, another material can be appropriately used for the scatterer 15 as long as it is a material that causes multiple scattering of a passing particle beam such as an acrylic plate. When a particle beam collides with this scatterer 15, the particles are scattered with a certain scattering angle depending on the material and the thickness of the scatterer 15. Before and after scattering, the position and momentum of the particles change. When the scatterer is sufficiently thin, the positional change is small and negligible, and it can be approximated that only the momentum varies before and after scattering.

In the present embodiment, the respective emittances in the orthogonal directions x and y of the particle beam are made uniform after scattering, and material and thickness of the scatterer 15 are set such that anisotropy of emittance is eliminated in the orthogonal directions (x, y) of the particle beam. Furthermore, by eliminating the anisotropy of the betatron function in the orthogonal directions (x, y) of the particle beam, it is possible to obtain beam characteristics in which the cross-sectional shape is substantially circular.

Additionally, taking notice to the distribution of the charged particles, it is also possible to align the distribution of the particle beam in the orthogonal directions (x, y) to the Gaussian distribution and eliminate non-uniformity. Thereby, it is possible to introduce a particle beam having uniform characteristics and a substantially circular cross-sectional shape at the upstream end of the segment 20a located at the most upstream and to freely transport particle beams to different height levels depending on the subsequent segment.

Figure 8:
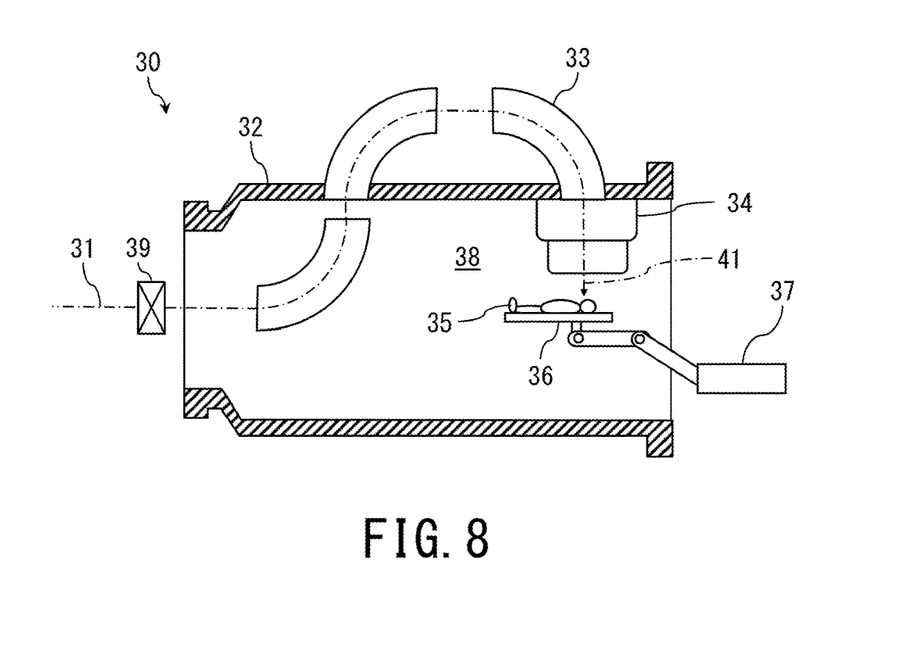
FIG. 8 is a longitudinal cross-sectional view illustrating the gantry-type irradiation equipment for irradiating a patient with a particle beam.

As shown in FIG. 8, the gantry-type irradiation equipment 30 includes a gantry 32, a beam transport system 33, an irradiation nozzle 34, and a movement controller 37. The gantry 32 has a treatment space 38 therein, and is rotationally displaced about its rotation axis 31 by its rotation driver (not shown). The beam transport system 33 is fixed to the gantry 32, and is rotatably provided at the end of the branch line 22 (FIG. 3) via a joint 39. The irradiation nozzle 34 irradiates the treatment space 38 with the particle beam 41 transported by the beam transport system 33 from the radial direction of the gantry 32. The movement controller 37 moves the bed 36 on which the patient 35 is placed, and sets the position and direction in the treatment space 38.

Since the irradiation equipment 30 is configured as described above, it is possible to bend the trajectory of the particle beam 41 inputted along the rotation axis 31 of the gantry 32 by 90° and to irradiate the patient 35 with this particle beam 41 from an arbitrary direction orthogonal to the rotation axis 31.

According to the present embodiment, since there is no anisotropy in the characteristics in the orthogonal directions (x, y) of the particle beam passing through the end of each segment 20 connected to the joint 39 and the cross-sectional shape of the particle beam is substantially circular, a constant beam quality is maintained independently of the rotation of the gantry 32.

Although a description has been given of the case where all of the plural irradiation equipments 30 to be disposed are the gantry-type in the present embodiment, all or some of the irradiation equipments 30 may be replaced by the fixed-type irradiation equipments. Since the characteristics and cross-sectional shape of the particle beam are substantially the same at both ends of each segment 20, there are compatible points between the gantry-type and the fixed-type. Thus, in the case of arranging the irradiation equipments 30 at the respective ends of the segments 20, there is no need to newly design a beam line and the degree of freedom of arrangement increases. Likewise, in the case of extension and reconstruction such as extension of a beam line or installing a new irradiation equipment, by newly arranging an additional segment 20 and an additional irradiation equipment 30 at the terminal of the segments 20, there is no need to newly design a beam line and it is possible to easily realize the extension and reconstruction with shorter construction period and lower cost.

According to the particle beam transport system of at least one embodiment as described above, since the characteristics and cross-sectional shape of the particle beam are substantially the same at both ends of each of the plural segments, it is possible to easily transport a high-quality beam to an arbitrary place. Hence, it is possible to facilitate beamline design of a particle beam treatment facility provided with plural treatment rooms accommodating irradiation equipments and to facilitate design and manufacture of the equipment, field adjustment, and extension and reconstruction of this facility, and thus it is possible to shorten its construction period and to reduce its construction cost.

Whereas a few embodiments of the present invention have been described, these embodiments are presented only by way of example, and not intended to limit the scope of the invention. These embodiments can be implemented in various other forms, and various omissions, replacements, changes, and combinations can be made without departing from the spirit of the invention. These embodiments and modifications thereof are included in the spirit and scope of the invention as well as in the invention set forth in the appended claims and the scope of equivalents thereof.

The invention claimed is:

1. A particle beam transport system comprising:
   a main line configured to transport a particle beam generated by an accelerator outward;
   a branch line branching from the main line;
   irradiation equipments provided at respective ends of the branch line and configured to irradiate a patient with the particle beam,
   wherein at least a part of the main line and the branch line is configured as plural segments; and
   in each of the segments, constituent components and arrangement of the constituent components are made common, and at least a first bending electromagnet, a focus electromagnet, and a second bending electromagnet among the constituent components are arranged in this order, the focus electromagnet configured to focus an outer diameter of the particle beam by an action of a magnetic field and the bending electromagnet configured to bend a traveling direction of the particle beam by an action of a magnetic field;
   beam characteristics of the particle beam of each of the plural segments are substantially equal at both ends.

2. The particle beam transport system according to claim 1,
   wherein in each of the plural segments a betatron function $\beta$ ($\beta x$, $\beta y$) in the orthogonal direction (x, y) of the passing particle beam is equal at both ends.

3. The particle beam transport system according to claim 1,
   wherein each of the plural segments includes a beam measuring component; and
   the beam measuring component is provided at a most upstream portion or a most downstream portion of each of the plural segments.

4. The particle beam transport system according to claim 1,
   wherein each of the plural segments includes a beam-trajectory correction electromagnet.

5. The particle beam transport system according to claim 1, further comprising a scatterer provided on the main line between the accelerator and one of the plural segments that is closest to the accelerator,
   the scatterer is configured to cause multiple scattering of the particle beam; and
   a cross-sectional shape of the particle beam at both ends of each of the plural segments is adjusted to be substantially circular.

6. The particle beam transport system according to claim 1,
   wherein phase difference of the particle beam between both ends of each of the plural segment is adjusted to be an integral multiple of 180 degrees.

7. The particle beam transport system according to claim 1,
   wherein the plural segments constitute the respective ends of the branch line and are connected to respective irradiation equipments.

8. A segment of a particle beam transport system that includes a main line transporting a particle beam generated by an accelerator outward, a branch line branching from the main line, and irradiation equipments provided at respective ends of the branch line and configured to irradiate a patient with the particle beam, the segment being used for the particle beam transport system by being connected to at least one segment of same configuration and comprising:
- an entrance on which the particle beam is made incident;
- a passage through which the particle beam made incident from the entrance advances; and
- an exit from which the particle beam having advanced through the passage is emitted,
- wherein plural magnets are arranged in such a manner that beam characteristics of the particle beam are substantially equal at the entrance and at the exit,
- in the segment, constituent components and arrangement of the constituent components are made common, and at least a first bending electromagnet, a focus electromagnet, and a second bending electromagnet among the constituent components are arranged in this order, the focus electromagnet configured to focus an outer diameter of the particle beam by an action of a magnetic field and the bending electromagnet configured to bend a traveling direction of the particle beam by an action of a magnetic field.

\* \* \* \* \*